United States Patent [19]
Isobe et al.

[11] Patent Number: 5,420,680
[45] Date of Patent: May 30, 1995

[54] METHOD FOR MEASURING REFRACTIVE INDEX AND THICKNESS OF FILM AND APPARATUS THEREFOR

[75] Inventors: Tami Isobe, Yokohama; Tsuyoshi Nakayama, Tokyo, both of Japan

[73] Assignee: Ricoh Company, Ltd., Tokyo, Japan

[21] Appl. No.: 103,825

[22] Filed: Aug. 9, 1993

Related U.S. Application Data

[63] Continuation of Ser. No. 788,445, Nov. 6, 1991, abandoned.

[30] Foreign Application Priority Data

Nov. 16, 1990 [JP] Japan ................. 2-310955

[51] Int. Cl.⁶ .................. G01N 21/41; G01N 21/21
[52] U.S. Cl. ................. 356/128; 356/369; 250/225
[58] Field of Search .......... 356/128, 364–370, 356/361, 381, 382; 250/225

[56] References Cited

U.S. PATENT DOCUMENTS

| | | | |
|---|---|---|---|
| 4,672,196 | 6/1987 | Canino | 250/225 |
| 4,695,162 | 9/1987 | Itonaga | 356/369 |
| 4,792,227 | 12/1988 | Yoshizawa | 356/128 |
| 4,806,776 | 2/1989 | Kley | 250/560 |
| 4,906,844 | 3/1990 | Hall | 250/225 |
| 4,983,823 | 1/1991 | Isobe | 250/225 |
| 5,073,026 | 12/1991 | Isobe | 356/369 |
| 5,096,298 | 3/1992 | Isobe | 356/369 |
| 5,107,105 | 4/1992 | Isobe | 250/225 |
| 5,108,185 | 4/1992 | Mansuripur et al. | 356/369 |

FOREIGN PATENT DOCUMENTS 3834948 8/1989 Germany ............ G01N 21/41

OTHER PUBLICATIONS

Applied Optics, vol. 19, No. 7, Apr. 1, 1980, pp. 1031–1033.
Philips Technische Rundschau, Ein schnelles Refraktometer Fur Dunne Aufdampfschichten 35; 1975/76; Nr. 3, pp. 70–71.
R. Mittra, "A Method For Measuring The Refractive Index Profile Of Thin–Film Waveguides", IEEE Transactions on Microwave Theory and Techniques, Jan. 1975, vol. MTT-23, pp. 176–177.
A. J. Warnecke, et al., "Refractive Index Dispersion In Semiconductor–related Thin Films", IBM J. Res. Develop., May 1973, pp. 256–262.
J. Raif, et al., "Rapid nondestructive method for measuring the refractive index and thickness of thin dielectric films", J. Phys., 1973, vol. 6, pp. 48–50.
N. J. Harrick, "Determination of Refractive Index and Film Thickness from Interference Fringes", Applied Optics, Oct. 1971, vol. 10, No. 10, pp. 2344–2349.

Primary Examiner—Hoa Q. Pham
Attorney, Agent, or Firm—Cooper & Dunham

[57] ABSTRACT

In method and apparatus for measuring a refractive index and a thickness of a thin film formed on a substrate, the thin film has m ($m \geq 1$) layers and a transparent uppermost layer is set as a first layer. A total of ($3m+1$) parameters include a refractive index $n(0)$ of an incident medium, a refractive index $n(j)$ ($j=1$ to m) of a j-th layer, absorption coefficients $k(j)$ ($j=2$ to m) of second to m-th layers, a refractive index $n(m+1)$ and an absorption coefficient $k(m+1)$ of the substrate, and thicknesses $d(j)$ ($j=2$ to m) of the second to m-th layers. Arbitrary one of the ($3m+1$) parameters is unknown and the other $3m$ parameters are known. This method and apparatus measure the unknown parameter. Monochromatic light having a wavelength is incident to the film having the m-layers at a predetermined incident angle from a first layer side in the incident medium to measure reflectances about S and P polarized light. A function of the unknown parameter is specified using measured values of the reflectances, the wavelength and $3m$ known parameters. An equation about this function is numerically solved to determine the unknown parameter.

14 Claims, 4 Drawing Sheets

METHOD FOR MEASURING REFRACTIVE INDEX AND THICKNESS OF FILM AND APPARATUS THEREFOR

This is a continuation of application Ser. No. 07/788,445 filed Nov. 6, 1991, now abandoned.

BACKGROUND OF THE INVENTION

1. Field of the Invention

The present invention relates to a method for measuring a refractive index and a thickness of a thin film and an apparatus therefor.

2. Description of the Related Art

There are many semiconductor devices and optical devices in which a thin film is formed. It is important to accurately measure a refractive index of the thin film, a film thickness, etc. with respect to performance of these devices.

In an ellipsometry known as a method for accurately measuring the refractive index and thickness of the thin film, a complicated large-sized device is required when the refractive index and thickness of the thin film are measured. For example, in Japanese Patent Application Laying Open (KOKAI) No. 2-75985, the inventors of this application proposed a series of measuring methods instead of the ellipsometry.

In such general measuring methods, monochromatic light is basically irradiated onto a thin film formed on a substrate to measure a reflectance of each of S-polarized light and P-polarized light. The refractive index of the thin film is calculated by numerically solving a predetermined equation based on the measured reflectance of each of the S-polarized light and the P-polarized light. An arc cosine function is included in this equation used in a numerical calculation. This arc cosine function is greatly changed with respect to a change in refractive index of the thin film as a measured object so that the calculation must be made with very high accuracy in a certain case. Further, only the refractive index of an uppermost layer is measured when the thin film is composed of a plurality of layers.

SUMMARY OF THE INVENTION

It is therefore an object of the present invention to provide novel method and apparatus for measuring a refractive index and a thickness of a thin film, in which no calculation is especially made with high accuracy and the thin film can be accurately measured and the range of a measured object is wide.

The above object of the present invention can be achieved by a method for measuring a refractive index and a thickness of a thin film formed on a substrate, in which the: thin film has m (m≧1) layers and a transparent uppermost layer is set as a first layer; a total of (3m+1) parameters include a refractive index n(0) of an incident medium, a refractive index n(j) (j=1 to m) of a j-th layer, absorption coefficients k(j) (j=2 to m) of second to m-th layers, a refractive index n(m+1) of the substrate, an absorption coefficient k(m+1) of the substrate, and thicknesses d(j) (j=2 to m) of the second to m-th layers; and arbitrary one of the (3m+1) parameters is unknown and the other 3m parameters are known. This method measures the unknown parameter X and comprises the steps of making monochromatic light having a wavelength λ incident to the thin film having the m-layers at a predetermined incident angle θ(0) from a first layer side in the incident medium; measuring reflectances Rs and Rp of S-polarized light and P-polarized light; specifying a function of the unknown parameter X by measured values of the reflectances Rs and Rp, the wavelength λ and 3m known parameters; and solving numerically an equation with respect to this function to determine a value of the unknown parameter X.

In the method, the above function is $F(X) = a + b + c$ and the above equation is represented by $F(X) = 0$ and a, b and c in this function $F(X)$ are respectively set as follows.

$$a = \rho^2(01s)\,\rho^2(12s)\,\rho^4(12p)\,\{1 - Rp\,\rho^2(01p)\}^2\,(As^2 + Bs^2) +$$

$$\rho^2(01p)\,\rho^2(12p)\,\rho^4(12s)\,\{1 - Rs\,\rho^2(01s)\}^2\,(Ap^2 + Bp^2) +$$

$$2\,\rho(01p)\,\rho^3(12p)\,\rho(01s)\,\rho^3(12s)\{1 - Rp\,\rho^2(01p)\}\,\{1 -$$

$$Rs\,\rho^2(01s)\}\,(ApAs + BpBp)$$

$$b = 2\,\rho^2(01s)\,\rho^2(12s)\,\rho^2(12p)\,\{\rho^2(01p) - Rp\}\,\{1 -$$

$$Rp\,\rho^2(01p)\}\,(As^2 + Bs^2) + 2\,\rho^2(01s)\,\rho^2(12s)\,\rho^2(12p)$$

$$\{\rho^2(01p) - Rp\}\{1 - Rp\,\rho^2(01p)\}\,(As^2 + Bs^2) -$$

$$2\,\rho(01p)\,\rho(12p)\,\rho(01s)\,\rho^3(12s)\,\{\rho^2(01p) - Rp\}$$

$$\{1 - Rs\,\rho^2(01s)\}(ApAs + BpBs) -$$

$$2\,\rho(01p)\,\rho^3(12p)\,\rho(01s)\,\rho(12s)\{\rho^2(01s) - Rs\}$$

$$\{1 - Rp\,\rho^2(01p)\}\,(ApAs + BpBs) -$$

$$4\,\rho^2(01p)\,\rho^2(12p)\,\rho^2(01s)\,\rho^2(12s)\,(ApBs - BpAs)^2$$

$$c = \rho^2(01s)\,\rho^2(12s)\,(\rho^2(01p) - Rp)^2\,(As^2 + Bs^2) +$$

$$\rho^2(01p)\,\rho^2(12p)\,\{\rho^2(01s) - Rs\}^2\,(Ap^2 + Bp^2) -$$

$$2\,\rho(01p)\,\rho(12p)\,\rho(01s)\,\rho(12s)\,\{\rho^2(01p) - Rp\}$$

$$\{\rho^2(01s) - Rs\}\,(ApAs + BpBs)$$

Ap, Bp, As and Bs in the formulas of a, b and are respectively set as follows.

$$Ap = Rp\,\cos\{\phi(01p) + \phi(12p)\} - \cos\{\phi(01p) - \phi(12p)\}$$

$$Bp = Rp\,\sin\{\phi(01p) + \phi(12p)\} - \sin\{\phi(01p) - \phi(12p)\}$$

$$As = Rs\,\cos\{\phi(01s) + \phi(12s)\} - \cos\{\phi(01s) - \phi(12s)\}$$

$$Bs = Rs\,\sin\{\phi(01s) + \phi(12s)\} - \sin\{\phi(01s) - \phi(12s)\}$$

$\rho(01p)$, $\rho(01s)$, $\rho(12p)$, $\rho(12s)$ and $\phi(01p)$, $\phi(01s)$, $\phi(12p)$, $\phi(12s)$ in the formulas of a, b and c are respectively set as follows.

$$r(01p) \equiv \rho(01p)\,\exp\{i\phi(01p)\}$$

$$r(01s) \equiv \rho(01s)\,\exp\{i\phi(01s)\}$$

$$r'(12p) \equiv \rho(12p)\,\exp\{i\phi(12p)\}$$

$$r'(12s) \equiv \rho(12s)\,\exp\{i\phi(12s)\}$$

r(01p) and r(01s) are respectively set to amplitude reflectances of the P-polarized light and the S-polarized light on an interface between the incident medium and the first layer.

r'(12p) and r'(12s) are respectively set to amplitude reflectances of the P-polarized light and the S-polarized light provided when the monochromatic light is incident to (m−1)-thin film layers except for the first layer in the incident medium having the same refractive index as the refractive index of the first layer.

Further, the above object of the present invention can be also achieved by an apparatus for measuring a refractive index and a thickness of a thin film formed on a substrate, in which the thin film has m (m≧1) layers and a transparent uppermost layer is set as first layer; a total of (3m+1) parameters include a refractive index n(0) of an incident medium, refractive index n(j) (j=1 to m) of a j-th layer, absorption coefficients k(j) (j=2 to m) of second to m-th layers, a refractive index n(m+1) of the substrate, an absorption coefficient k(m+1) of the substrate, and thicknesses d(j) (j=2 to m) of the second to m-th layers; and arbitrary one of the (3m+1) parameters is unknown and the other 3m parameters are known. This apparatus measures the unknown parameter X and comprises support means for supporting a measured sample; a light source device for selectively irradiating a monochromatic beam of each of S-polarized light and P-polarized light to the measured sample at a predetermined incident angle; photoelectric converting means for receiving a light beam reflected from the measured sample and photoelectrically converting this light beam; and a computer for calculating a predetermined equation based on an output of the photoelectric converting means. This predetermined equation can be set to the above-mentioned F(X)=0 in the method for measuring the refractive index and thickness of the thin film.

In the above-mentioned method and apparatus, no calculation is especially made with high accuracy and the thin film can be accurately measured and the range of a measured object is wide.

Further objects and advantages of the present invention will be apparent from the following description of the preferred embodiments of the present invention as illustrated in the accompanying drawings.

DESCRIPTION OF THE PREFERRED EMBODIMENTS

Figure 1:
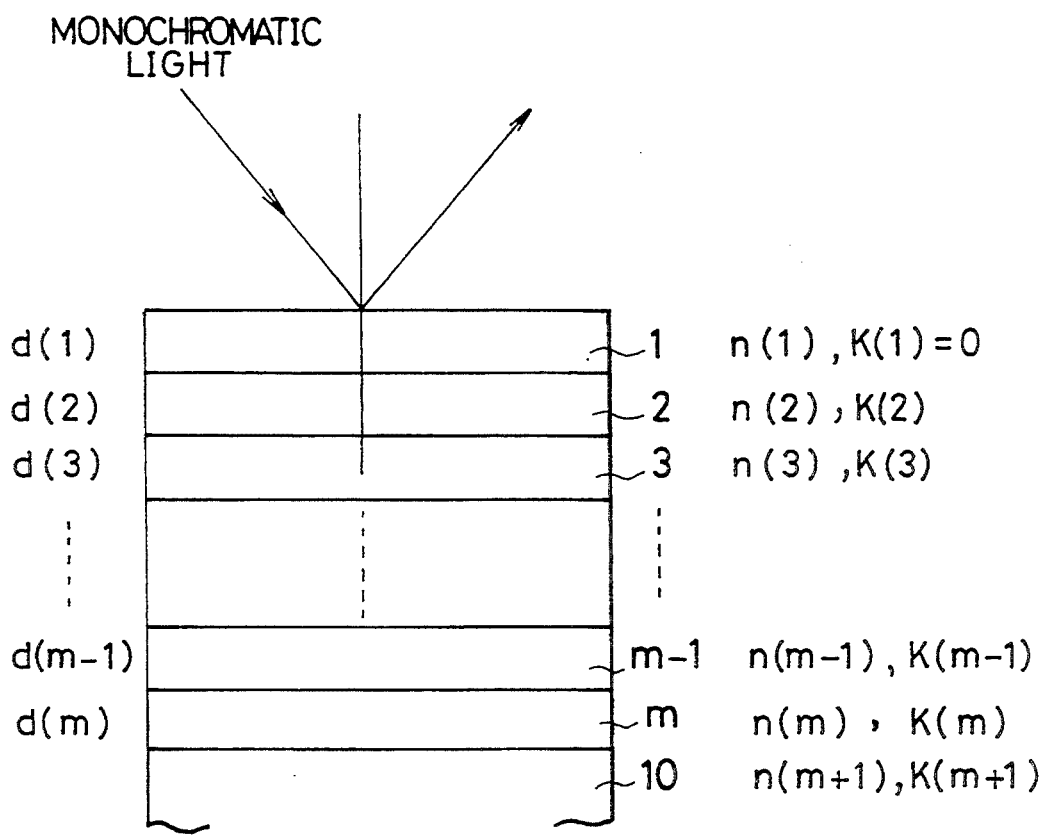
FIGS. 1 and 2 are views for explaining the principle of the present invention.

The preferred embodiments of a method and an apparatus in the present invention will next be described in detail with reference to the accompanying drawings.

In a method for measuring a refractive index and a thickness of a thin film according to the present invention, a thin film having m (m≧1) layers is formed on a substrate and a transparent uppermost layer is set as a first layer. A total of (3m+1) parameters include a refractive index n(0) of an incident medium, a refractive index n(j) (j=1 to m) of a j-th layer, absorption coefficients k(j) (j=2 to m) of second to m-th layers, a refractive index n(m+1) of the substrate, an absorption coefficient k(m+1) of the substrate, and thicknesses d(j) (j=2 to m) of the second to m-th layers. Arbitrary one of the (3m+1) parameters is unknown and the other 3m parameters are known. The method of the present invention measures the unknown parameter X and has the following features.

Namely, monochromatic light having a wavelength λ is incident to the thin film having the m-layers at a predetermined incident angle θ(0) from a first layer side in the incident medium. Reflectances Rs and Rp of S-polarized light and P-polarized light are then measured.

A function F(X)=a+b+c with respect to an unknown parameter X is specified by measured values of the reflectances Rs and Rp, the wavelength λ and 3m known parameters. An equation F(X)=0 is then solved numerically with respect to the unknown parameter X to specify the unknown parameter X.

Values a, b and c on the right-hand side of this function F(X) are respectively provided as follows.

$$a = \rho^2(01s)\,\rho^2(12s)\,\rho^4(12p)\,\{1 - Rp\,\rho^2(01p)\}^2\,(As^2 + Bs^2) +$$

$$\rho^2(01p)\,\rho^2(12p)\,\rho^4(12s)\,\{1 - Rs\,\rho^2(01s)\}^2\,(Ap^2 + Bp^2) +$$

$$2\,\rho(01p)\,\rho^3(12p)\,\rho(01s)\,\rho^3(12s)\{1 - Rp\,\rho^2(01p)\}\,\{1 -$$

$$Rs\,\rho^2(01s)\}\,(ApAs + BpBp)$$

$$b = 2\,\rho^2(01s)\,\rho^2(12s)\,\rho^2(12p)\,\{\rho^2(01p) - Rp\}\,\{1 -$$

$$Rp\,\rho^2(01p)\}\,(As^2 + Bs^2) + 2\,\rho^2(01s)\,\rho^2(12s)\,\rho^2(12p)$$

$$\{\rho^2(01p) - Rp\}\{1 - Rp\,\rho^2(01p)\}\,(As^2 + Bs^2) -$$

$$2\,\rho(01p)\,\rho(12p)\,\rho(01s)\,\rho^3(12s)\,\{\rho^2(01p) - Rp\}$$

$$\{1 - Rs\,\rho^2(01s)\}(ApAs + BpBs) -$$

$$2\,\rho(01p)\,\rho^3(12p)\,\rho(01s)\,\rho(12s)\{\rho^2(01s) - Rs\}$$

$$\{1 - Rp\,\rho^2(01p)\}\,(ApAs + BpBs) -$$

$$4\,\rho^2(01p)\,\rho^2(12p)\,\rho^2(01s)\,\rho^2(12s)\,(ApBs - BpAs)^2$$

$$c = \rho^2(01s)\,\rho^2(12s)\,(\rho^2(01p) - Rp)^2\,(As^2 + Bs^2) +$$

$$\rho^2(01p)\,\rho^2(12p)\,\{\rho^2(01s) - Rs\}^2\,(Ap^2 + Bp^2) -$$

$$2\,\rho(01p)\,\rho(12p)\,\rho(01s)\,\rho(12s)\,\{\rho^2(01p) - Rp\}$$

$$\{\rho^2(01s) - Rs\}\,(ApAs + BpBs)$$

Ap, Bp, As and Bs in the formulas of a, b and c are respectively set as follows.

$Ap = Rp \cos\{\phi(01p) + \phi(12p)\} - \cos\{\phi(01p) - \phi(12p)\}$ $Bp = Rp \sin\{\phi(01p) + \phi(12p)\} - \sin\{\phi(01p) - \phi(12p)\}$ $As = Rs \cos\{\phi(01s) + \phi(12s)\} - \cos\{\phi(01s) - \phi(12s)\}$ $Bs = Rs \sin\{\phi(01s) + \phi(12s)\} - \sin\{\phi(01s) - \phi(12s)\}$ $\rho(01p)$, $\rho(01s)$, $\rho(12p)$, $\rho(12s)$ and $\phi(01p)$, $\phi(01s)$, $\phi(12p)$, $\phi(12s)$ in the formulas of a, b and c are respectively set as follows.

$r(01p) \equiv \rho(01p)\exp\{i\phi(01p)\}$ $$r(o1s) = \rho(01s) \exp\{i\phi(01s)\}$$

$$r'(12p) = \rho(12p) \exp\{i\phi(12p)\}$$

$$r'(12s) = \rho(12s) \exp\{i\phi(12s)\}$$

In these formulas, r(01p) and r(01s) are respectively set to amplitude reflectances of the P-polarized light and the S-polarized light on an interface between the incident medium and the first layer.

Further, r'(12p) and r'(12s) are respectively set to amplitude reflectances of the P-polarized light and the S-polarized light provided when the monochromatic light is incident to (m−1)-thin film layers except for the first layer in the incident medium having the same refractive index as the refractive index of the first layer.

The unknown parameter X can be set to the refractive index of one of the thin film layers, the substrate, or the incident medium. Further, the unknown parameter X can be set to the absorption coefficient of the substrate or one of the thin film layers except for the first layer.

Otherwise, the unknown parameter X can be set to the thickness of the thin film layers except for the first layer.

When the first thin film layer is transparent, no light having the measured wavelength λ is absorbed by the first thin film layer.

An apparatus for measuring a refractive index and a thickness of a thin film according to the present invention is used to execute the above method for measuring a refractive index and a thickness of a thin film and has a support means, a light source device, a photoelectric converting means and a computer.

The support means supports a measured sample.

The light source device selectively irradiates a monochromatic beam of each of S-polarized light and P-polarized light to the measured sample at a predetermined incident angle.

The photoelectric converting means receives a light beam reflected from the measured sample and photoelectrically converts this light beam.

The computer calculates the above-mentioned equation F(X)=0 based on an output of the photoelectric converting means.

The method and apparatus of the present invention can be used when the number m of thin film layers is equal to one or more.

In FIG. 1, reference numeral 10 designates a substrate.

Thin film layers 1 to m are sequentially formed on the substrate 10. An uppermost layer is formed as a first layer 1. A j-th thin film layer (j=1 to m) is counted from an uppermost layer side. Parameters n(j), k(j), d(j) (j=1 to m) respectively designate a refractive index, an absorption coefficient and a thickness of the j-th thin film layer.

Parameters n(m+1) and k(m+1) respectively designate a refractive index and an absorption coefficient of the substrate 10. Further, parameter n(0) designates the refractive index of an incident medium.

The three parameters of the refractive index, the absorption coefficient and the thickness are provided with respect to each of the m thin film layers. Accordingly, a total of (3m+3) parameters are obtained by adding these 3m parameters, two parameters about the substrate 10, and one parameter about the incident medium. The first thin film layer 1 is transparent so that the absorption coefficient k(1) of this film layer is zero.

Further, as described later, the thickness d(1) of the first thin film layer 1 is an indefinite value in a measuring principle of the present invention. Accordingly, the number of parameters in the layer structure shown in FIG. 1 is reduced and is substantially set to 3m+1 by subtracting number 2 about k(1) and d(1) from the above number (3m+3).

In an operating state of the layer structure shown in FIG. 1, monochromatic light having a wavelength λ is incident to the first thin film layer at an incident angle θ(0). At this time, amplitude reflectances r(p) and r(s) of S-polarized light and P-polarized light are represented in accordance with the following description.

Figure 2:
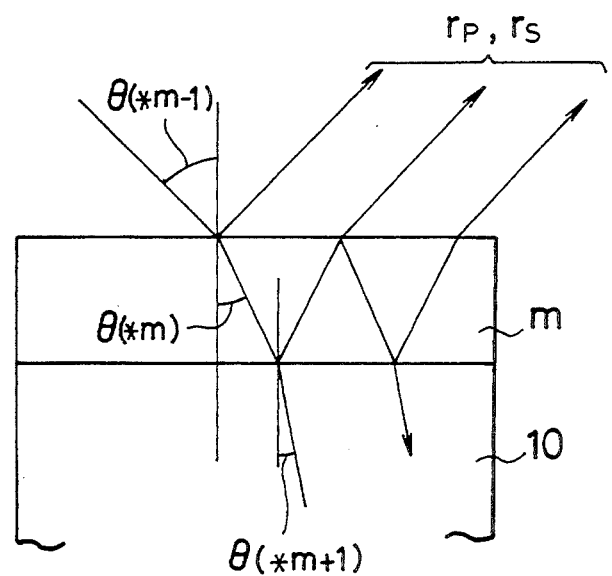

FIG. 2 shows a state in which only the m-th thin film layer m shown in FIG. 1 is formed on the substrate 10.

The amplitude reflectances r(p) and r(s) are represented as follows when the monochromatic light having wavelength λ is incident to the layer structure in an incident medium having the same refractive index and absorption coefficient as the (m−1)-th thin film layer and the incident angle of this monochromatic light is set to θ(*m−1).

$$r(p) = [r(m-1,m:p) + r(m,m+1:p)\exp\{-2i\beta(*m)\}] / \qquad (1)$$

$$[1 + r(m-1,m:p)r(m,m+1:p)\exp\{-2i\beta(*m)\}]$$

$$r(s) = [r(m-1,m:s) + r(m,m+1:s)\exp\{-2i\beta(*m)\}] / \qquad (2)$$

$$[1 + r(m-1,m:s)r(m,m+1:s)\exp\{-2i\beta(*m)\}]$$

In the above formulas (1) and (2), reference numerals p and s respectively designate the P-polarized incident light and the S-polarized incident light. Reference numeral r(m−1,m:p) designates a Fresnel's reflection coefficient on an interface between the thin film layer m and the incident medium in the case of the P-polarized incident light. Reference numeral r(m,m+1:p) designates a Fresnel's reflection coefficient on an interface between the thin film layer m and the substrate 10 in the case of the P-polarized incident light.

Similarly, reference numeral r(m−1,m:s) designates a Fresnel's reflection coefficient on the interface between the thin film layer m and the incident medium in the case of the S-polarized incident light. Reference numeral r(m,m+1:s) designates a Fresnel's reflection coefficient on the interface between the thin film layer m and the substrate 10 in the case of the S-polarized incident light.

These reflection coefficients are provided as follows.

$$r(m-1,m:p) = \qquad (3)$$

$$[n(*m)\cos(\theta*m-1) - n(*m-1)\cos(\theta*m)]/$$

$$[n(*m)\cos(\theta*m-1) + n(*m-1)\cos(\theta*m)]$$

$$r(m-1,m:s) = \qquad (4)$$

$$[n(*m-1)\cos(\theta*m-1) - n(*m)\cos(\theta*m)]/$$

$$[n(*m-1)\cos(\theta*m-1) + n(*m)\cos(\theta*m)]$$

$$r(m,m+1:p) = \qquad (5)$$

$$[n(*m+1)\cos(\theta*m) - n(*m)\cos(\theta*m+1)]/$$

$$[n(*m+1)\cos(\theta*m) + n(*m)\cos(\theta*m+1)]$$

$$r(m,m+1:s) = \qquad (6)$$

-continued
$$[n(*m)\cos(\theta*m) - n(*m + 1)\cos(\theta*m + 1)]/$$
$$[n(*m)\cos(\theta*m) + n(*m + 1)\cos(\theta*m + 1)]$$

As shown in FIG. 2, $\theta*m-1$, $\theta*m$ and $\theta*m+1$ respectively designate an incident angle, an angle of refraction and an angle of refraction. This mark * shows a complex number. For example, the above reference numeral $n(*m)$ designates a complex refractive index of the thin film layer m and is represented as follows by using the refractive index $n(m)$ and the absorption coefficient $k(m)$.

$$n(*m) = n(m) - ik(m).$$

Reference numeral $2\beta(*m)$ used in above formulas (1) and (2) shows a change in phase of light caused while this light goes and returns at one time in the thin film layer m. This phase change $2\beta(*m)$ is provided as follows.

$$2\beta(*m) = 4\pi d(m)n(*m) \cos \{\theta(*m)\}/\lambda \quad (7)$$

In a state in which a thin film layer $(m-1)$ having a thickness $d(m-1)$ is formed on the thin film layer m shown in FIG. 2, the amplitude reflectances of monochromatic light will next be described when the monochromatic light having wavelength $\lambda$ is incident to the layer structure in the incident medium having the same refractive index and absorption coefficient as a thin film layer $(m-2)$ and the incident angle of this monochromatic light is set to $\theta(*m-2)$.

This state is considered as a state in which the thin film layer $(m-1)$ is formed on a substrate composed of a combination of the substrate 10 and the thin film layer m. The amplitude reflectances in this state are provided by respectively replacing suffix parameters $(m+1)$, m and $(m-1)$ with m, $(m-1)$ and $(m-2)$ in the above formulas (1) and (2). There are reflection coefficients $r(m-1,m:p)$ and $r(m-1,m:s)$ on the right-hand sides of the newly rewritten formulas and the reflection coefficients on the left-hand sides of the above formulas (3) and (4) are used as these reflection coefficients $r(m-1,m:p)$ and $r(m-1,m:s)$. Thus, it is possible to obtain correct amplitude reflectances.

The thin film layers are sequentially stacked with each other as mentioned above. The incident medium is repeatedly replaced with an incident medium having the complex refractive index of a thin film layer formed just on an uppermost laminated thin film layer. Finally, the amplitude reflectances in the light incident state shown in FIG. 1, i.e., the amplitude reflectances in the entire structure of the m thin film layers are provided by respectively replacing $r(1,2:p)$ and $r(1,2:s)$ with $r'(1,2:p)$ and $r'(1,2:s)$ in the following formulas (1') and (2') provided by setting number m to number 1 in the above formulas (1) and (2).

$$r(p) = [r(0,1:p) + r(1,2:p)\exp\{-2i\beta(*1)\}]/ \quad (1')$$
$$[1 + r(0,1:p)r(1,2:p)\exp\{-2i\beta(*1)\}]$$

$$r(s) = [r(0,1:s) + r(1,2:s)\exp\{-2i\beta(*1)\}]/ \quad (2')$$
$$[1 + r(0,1:s)r(1,2:s)\exp\{-2i\beta(*1)\}]$$

In this case, $r'(1,2:p)$ and $r'(1,2:s)$ are amplitude reflectances provided when the first thin film layer 1 is removed from the layer structure shown in FIG. 1 and the refractive index of the incident medium is changed to $n(1)$ and the monochromatic light having wavelength $\lambda$ is incident to the thin film layers at an incident angle $\theta(1)$.

Amplitude reflectances $r(0,1:p)$, $r(0,1:s)$, $r'(1,2:p)$ and $r(1,2:s)$ are briefly represented by $r(01p)$, $r(01s)$, $r'(12p)$ and $r'(12s)$ in the following description. In this case, the amplitude reflectances $r(p)$ and $r(s)$ to be obtained are provided as follows.

$$r(p) = [r(01p) + r'(12p)\exp\{-2i\beta(*1)\}]/ \quad (8)$$
$$[1 + r(01p)r'(12p)\exp\{-2i\beta(*1)\}]$$

$$r(s) = [r(01s) + r'(12s)\exp\{-2i\beta(*1)\}]/ \quad (9)$$
$$[1 + r(01s)r'(12s)\exp\{-2i\beta(*1)\}]$$

In the above formulas (8) and (9), the amplitude reflectances $r(01s)$, $r'(12s)$, $r(01p)$ and $r'(12p)$ are generally complex numbers. Therefore, these amplitude reflectances are represented as follows.

$$r(01s) = \rho(01s)\exp\{i(\phi(01s)\} \quad (10)$$
$$r(01p) = \rho(01p)\exp\{i(\phi(01p)\}$$
$$r'(12s) = \rho(12s)\exp\{i(\phi(12s)\} \quad (11)$$
$$r'(12p) = \rho(12p)\exp\{i(\phi(12p)\}$$

Further, $2\beta(*1)$ is set as follows.

$$2\beta(*1) = a(1)\{u(1) - iv(1)\}$$

Here, $a(1)$, $2u^2(1)$ and $2v^2(1)$ are respectively represented by the following formulas (12) to (14).

$$a(1) = 4\pi d(1)/\lambda \quad (12)$$
$$2u^2(1) = n^2(1) - k^2(1) - n^2(0)\sin^2\theta(0) + \quad (13)$$
$$\sqrt{[n^2(1) - k^2(1) - n^2(0)\sin^2\theta(0) + 4n^2(1)k^2(1)]}$$
$$2v^2(1) = -\{n^2(1) - k^2(1) - n^2(0)\sin^2\theta(0)\} + \quad (14)$$
$$\sqrt{[n^2(1) - k^2(1) - n^2(0)\sin^2\theta(0) + 4n^2(1)k^2(1)]}$$

In these formulas, symbol $\sqrt{[\ ]}$ designates a square root of a function within the bracket [ ].

Reflectances Rs and Rp of the S-polarized light and the P-polarized light are respectively represented as follows by products of amplitude reflectances $r(s)$ and $r(p)$ and complex conjugate amounts $r(*s)$ and $r(*p)$ thereof.

$$Rs = r(s)r(*s), Rp = r(p)r(*p)$$

These energy reflectivities Rp and Rs are calculated and provided as follows in accordance with the above formulas (8), (9), (10) and (11).

$$Rp = [\rho^2(01p) + \rho^2(12p)\exp\{-2a(1)v(1)\} + \quad (15)$$
$$2\rho(01p)\rho(12p)\exp\{-a(1)v(1)\}\cos\{\phi(01p) - \phi(12p) + a(1)u(1)\}]/$$
$$[1 + \rho^2(01p)\rho^2(12p)\exp\{-2a(1)v(1)\} +$$
$$2\rho(01p)\rho(12p)\exp\{-a(1)v(1)\}\cos\{\phi(01p) - \phi(12p) + a(1)u(1)\}]$$

$$Rs = [\rho^2(01s) + \rho^2(12s)\exp\{-2a(1)v(1)\} + \quad (16)$$
$$2\rho(01s)\rho(12s)\exp\{-a(1)v(1)\}\cos\{\phi(01s) - \phi(12s) + a(1)u(1)\}]/$$

-continued $$[1 + \rho^2(01s)\rho^2(12s)\exp\{-2\alpha(1)v(1)\} +$$
$$2\rho(01s)\rho(12s)\exp\{-\alpha(1)v(1)\}\cos\{\phi(01s) - \phi(12s) + \alpha(1)u(1)\}]$$

Further, when parameters $\rho$ and $\theta$ are respectively replaced with the following values, $$\rho \equiv \exp\{-\alpha(1)v(1)\}, \quad \theta \equiv \alpha(1)u(1),$$

the reflectances Rp and Rs in the formulas (15) and (16) are rewritten as follows.

$$Rp = [\rho^2(01p) + \rho^2(12p)\rho^2 + \qquad (15')$$
$$2\rho(01p)\rho(12p)\rho\cos\{\phi(01p) - \phi(12p) + \theta\}]/[1 +$$
$$\rho^2(01p)\rho^2(12p)\rho^2 + 2\rho(01p)\rho(12p)\rho\cos\{\phi(01p) - \phi(12p) + \theta\}]$$

$$Rs = [\rho^2(01s) + \rho^2(12s)\rho^2 + \qquad (16')$$
$$2\rho(01s)\rho(12s)\rho\cos\{\phi(01s) - \phi(12s) + \theta\}]/[1 +$$
$$\rho^2(01s)\rho^2(12s)\rho^2 + 2\rho(01s)\rho(12s)\rho\cos\{\phi(01s) - \phi(12s) + \theta\}]$$

The above-mentioned values Ap, Bp, As and Bs are respectively represented as follows.

$$Ap = Rp \cos\{\phi(01p)+\phi(12p)\} - \cos\{\phi(01p)-\phi(12p)\}$$

$$Bp = Rp \sin\{\phi(01p)+\phi(12p)\} - \sin\{\phi(01p)-\phi(12p)\}$$

$$As = Rs \cos\{\phi(01s)+\phi(12s)\} - \cos\{\phi(01s)-\phi(12s)\}$$

$$Bs = Rs \sin\{\phi(01s)+\phi(12s)\} - \sin\{\phi(01s)-\phi(12s)\}$$

When these values Ap, Bp, As and Bs are used, the above formulas (15') and (16') can be represented as follows.

$$Ap \cos\theta + Bp \sin\theta = Cp \qquad (17)$$

$$As \cos\theta + Bs \sin\theta = Cs \qquad (18)$$

In these formulas (17) and (18), values Cp and Cs are set as follows.

$$Cp = [\rho^2(01p) - Rp + \rho^2(12p)\rho^2\{1 - Rp\rho^2(01p)\}]/2\rho(01p)\rho(12p)$$

$$Cs = [\rho^2(01s) - Rs + \rho^2(12s)\rho^2\{1 - Rs\rho^2(01s)\}]/2\rho(01s)\rho(12s)$$

When $\sin\theta$ and $\cos\theta$ are calculated from the formulas (17) and (18) and the relation $(\sin\theta)^2 + (\cos\theta)^2 = 1$ is used, the following formula (17) is finally obtained by using the above values a, b, c and $\rho$.

$$a\rho^4 + b\rho^2 + c = 0 \qquad (17)$$

In the following defining formula of $\rho$, $$\rho \equiv \exp\{-\alpha(1)v(1)\},$$

k(1) in the formula (14) is equal to zero since the first thin film layer 1 is transparent with respect to light having a measured wavelength $\lambda$. Accordingly, v(1) provided on the left-hand side of the formula (14) is equal to zero. Therefore, $\rho = 1$ is identically formed and the above formula (17) is represented as follows.

$$a + b + c = 0 \qquad (18)$$

Since v(1) = 0 is formed, $\alpha(1)$ is indeterminate and the thickness d(1) of the first thin film layer 1 is also indeterminate in accordance with the formula (12).

Each of the constructional elements or values a, b and c in the equation (18) is apparently solved with respect to parameters n(0), n(j) (j = 1 to m+1), k(j) (j = 2 to m+1), d(j) (j = 2 to m), $\theta(0)$, $\lambda$, Rs and Rp in accordance with the above-mentioned defining formulas of a, b and c. These solved results are represented by the following formula.

$$F\{n(0), n(j), k(j), d(j), \theta(0), \lambda, Rs, Rp\} = 0$$

The 3m known parameters, the measured wavelength $\lambda$, the incident angle $\theta(0)$ and measured values of Rs and Rp are concretely substituted in this formula so that an equation F(X) = 0 is obtained. In this equation, only an unknown parameter X is a variable.

Accordingly, a value of the parameter X can be specified by numerically solving this equation.

Various kinds of known operating programs can be used to solve this equation with respect to the parameter X. It is sufficient to basically calculate the parameter X satisfying this equation by changing the value of the parameter X in fine steps and judging whether or not this equation is satisfied in each of the steps.

Concrete embodiments of the present invention will next be described.

Figure 3:
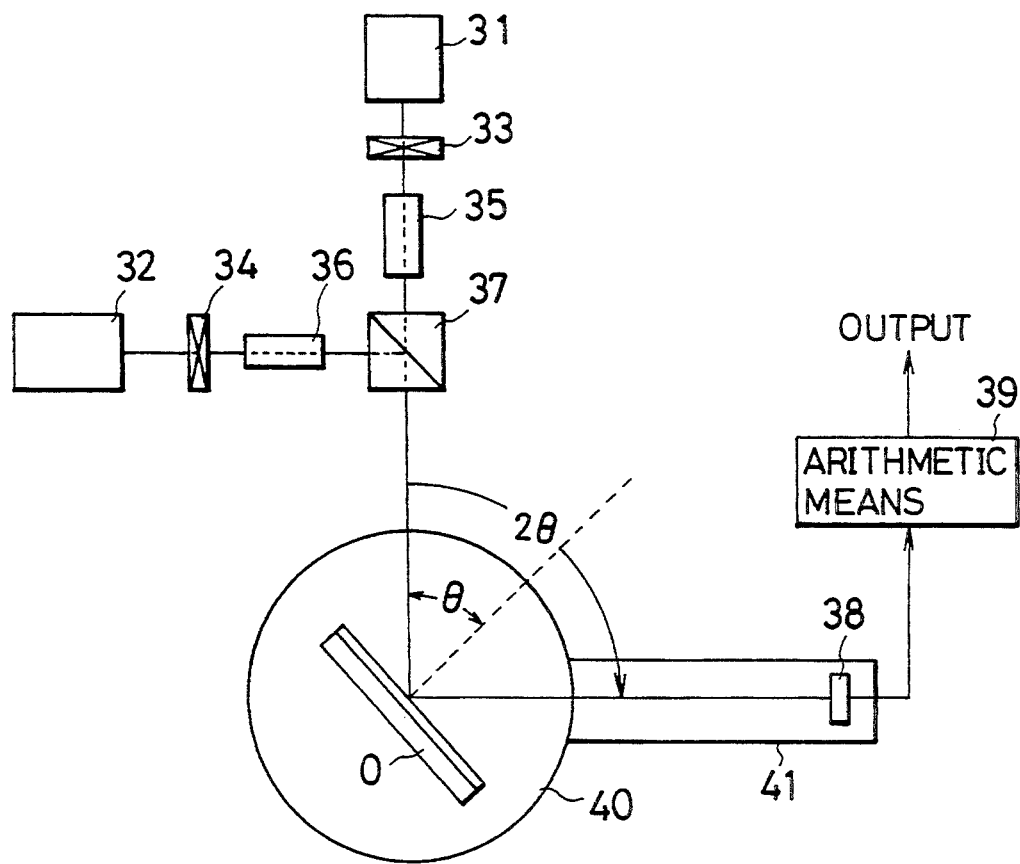
FIG. 3 is a view showing an apparatus for measuring a refractive index and a thickness of a thin film in accordance with one embodiment of the present invention.

FIG. 3 shows an apparatus for measuring a refractive index and a thickness of a thin film in accordance with one embodiment of the present invention.

In FIG. 3, each of laser beam sources 31 and 32 is constructed by a HeNe laser for providing a stable output at a wavelength 6328 Å. The laser beam sources 31 and 32 are used with respect to S-polarized light and P-polarized light provided by polarizers 35 and 36.

The S-polarized light and the P-polarized light are irradiated onto a measured sample 0 through a polarizing beam splitter 37 having a high extinction ratio. Shutters 33 and 34 can select one of S and P polarizing states of light irradiated onto the measured sample 0.

The laser beam sources 31, 32, the shutters 33, 34, the polarizers 35, 36 and the polarizing beam splitter 37 constitute a light source device. The measured sample 0 is supported by a turn table 40. A rotating arm 41 is coaxially attached to the turn table 40. When the rotating arm 41 is rotated angle $2\theta$, the turn table 40 is rotated angle $\theta$.

The turn table 40 and the rotating arm 41 constitute a support means.

A photo-sensor 38 is disposed as a photoelectric converting means at a free end of the rotating arm 41.

A computer 39 functionally has an amplifier for amplifying an output of the photo-sensor 38, a converter for converting an amplified signal to a digital signal, and a computing circuit for numerically solving the equation F(X) = 0 based on the converted digital signal. Further, the computer 39 functionally has a means for setting a numerical condition required for the computing circuit, and a means for displaying calculated results of the computing circuit. The computer 39 can be concretely realized by a computer system.

The computing circuit stores a general formula of the equation F(X) = 0 and programs for solving this equation. In this general formula, the used wavelength $\lambda$ is set to 6328 Å. With respect to angle $\theta(0)$, the angle $\theta$ of rotation of the turn table 40 is automatically set. The value of a known parameter with respect to the measured sample 0 is inputted from a keyboard partially constituting the computer. With respect to the measured values of Rs and Rp, an output or the photo-sensor 38 is directly inputted to the computer through an interface.

One measuring example using the thin film measuring apparatus shown in FIG. 3 will next be described. A measuring operation of the thin film measuring apparatus in this example is performed in a thin film measuring method in accordance with a second concrete embodiment of the present invention.

A silicon substrate is used and a thin film made of SiN is formed on this silicon substrate by a plasma CVD method. A thin film made of $SiO_2$ is formed by sputtering on the thin film made of SiN, thereby providing a measured sample 0.

With respect to the measured sample 0, the refractive index $n(1)$ of the first thin film layer made of $SiO_2$ is an unknown parameter.

The known parameters are provided as follows.

The refractive index and the absorption coefficient of the silicon substrate are respectively set as follows.
  refractive index: $n(3)=3.858$
  absorption coefficient: $k(3)=0.018$ The refractive index, the absorption coefficient and the thickness of the thin film made of SiN are respectively set as follows.
  refractive index: $n(2)=2.000$
  absorption coefficient: $k(2)=0.500$
  film thickness: $d(2)=500$ Å

The measured values of reflectances Rp and Rs at the incident angle $\theta(0)=56$ degrees are respectively provided as follows.

$$Rp=0.09423, Rs=0.01099$$

Figure 5:
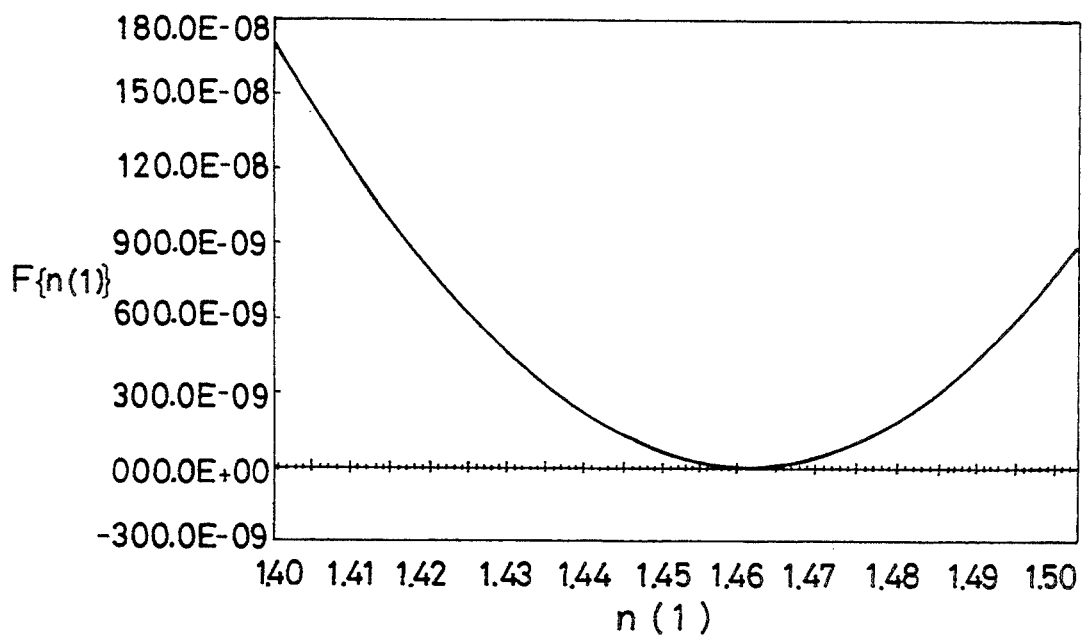
FIG. 5 is a graph for explaining a method for measuring a refractive index and a thickness of a thin film in accordance with one embodiment of the present invention.

When the value of $n(1)$ as an unknown parameter X is changed from 1.4 to 1.5 every 0.001, a value of the function $F(X)$ is changed as shown by a curve in FIG. 5. The equation $F(X)=0$ is satisfied when $X=1.460$.

Accordingly, the refractive index $n(1)$ can be specified and set to 1.460.

Figure 4:
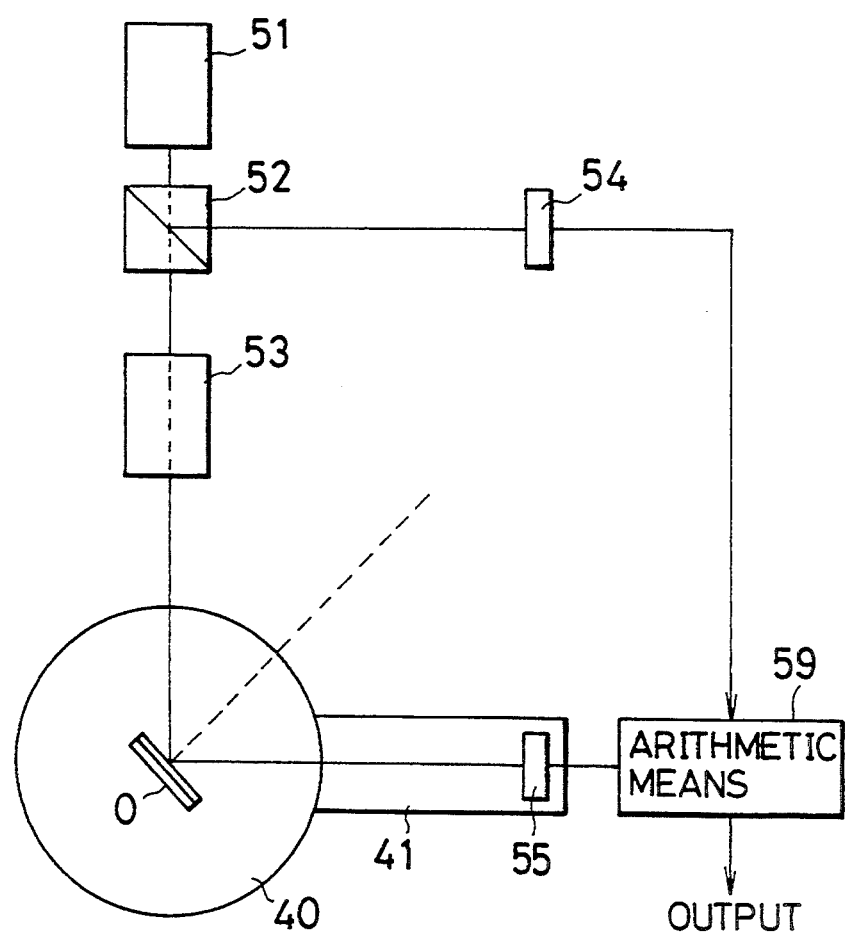
FIG. 4 is a view showing an apparatus for measuring a refractive index and a thickness of a thin film in accordance with another embodiment of the present invention.

FIG. 4 shows an apparatus for measuring a refractive index and a thickness of a thin film in accordance with another embodiment of the present invention.

In FIG. 4, light is emitted from a laser beam source 51 composed of a HeNe laser having a wavelength 6328 Å and is divided into two light portions by a beam splitter 52. One light portion is incident to a photo-sensor 54 to use this light portion for a monitor. The other light portion is irradiated onto a measured sample 0 through a polarizer 53. At this time, the light irradiated to the measured sample 0 can be set to S-polarized light or P-polarized light by rotating the polarizer 53.

In this embodiment, the laser beam source 51, the beam splitter 52, the polarizer 53 and the photo-sensor 54 constitute a light source device.

Similar to the case of the apparatus shown in FIG. 3, a support means for supporting the measured sample 0 is constructed by a turn table 40 and a rotating arm 41. A photo-sensor 55 is disposed as a photoelectric converting means at a free end of the rotating arm 41.

Outputs of the photo-sensors 54 and 55 are inputted to an arithmetic means 59. The computer 59 has a function of the computer 39 disposed in the apparatus shown in FIG. 3 and also has a monitoring function of the light source device. The intensity of light transmitted through the polarizer 53 is an intensity of light irradiated onto the measured sample. A ratio of this light intensity and a light-receiving intensity of the photo-sensor 54 is measured in advance and is inputted to the computer 59. When the light intensity in the light source device is changed during a measuring operation of the measured sample, a measured value of the measured sample is corrected by the above ratio.

One example of the measurement of a thin film using this measuring apparatus will next be described. A method for measuring a refractive index and a thickness of a thin film in accordance with a third embodiment of the present invention is used in this example.

A thin film made of $SiO_2$ and having a thickness 9114 Å is formed on a silicon substrate by thermal oxidation, thereby providing a measured sample.

An absorption coefficient $k(2)$ of the substrate is an unknown parameter with respect to this measured sample.

Known parameters with respect to this measured sample are provided as follows.

The refractive index of the silicon substrate is set as follows.
  refractive index: $n(2)=3.858$ The refractive index of the thin film made of $SiO_2$ is set as follows.
  refractive index: $n(1)=1.460$ The measured values of reflectances Rp and Rs at an incident angle $\theta(0)=60$ degrees are respectively provided as follows.

$$Rp=0.16351, Rs=0.16217$$

Figure 6:
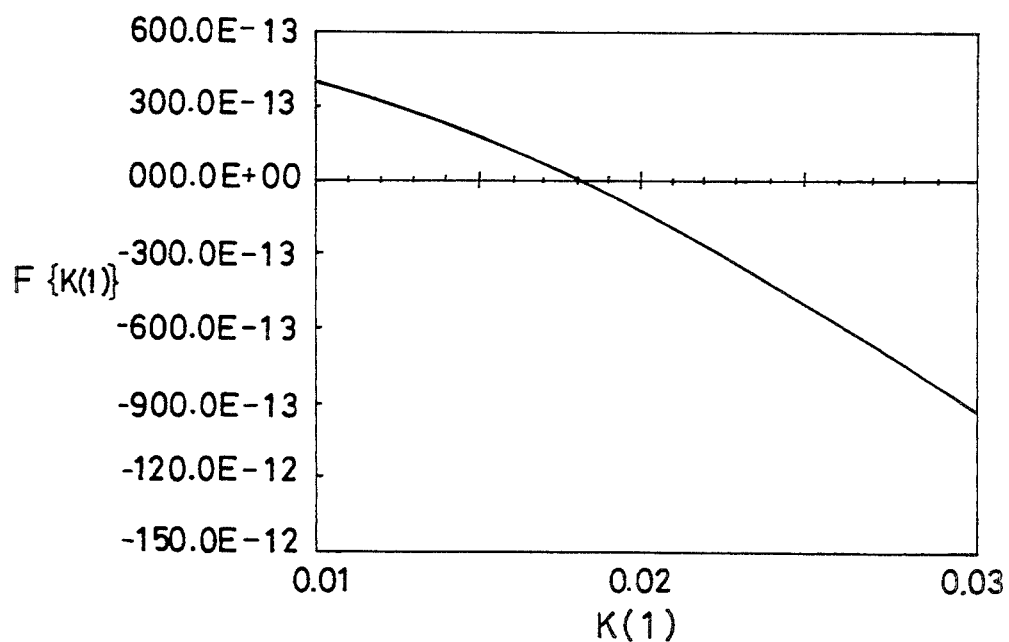
FIG. 6 is a graph for explaining a method for measuring a refractive index and a thickness of a thin film in accordance with another embodiment of the present invention.

When the value of $k(2)$ as an unknown parameter X is changed from 0.01 to 0.03 every 0.001, a value of the function $F(X)$ is changed as shown by a curve in FIG. 6. The equation $F(X)=0$ is satisfied when $X=0.018$.

Accordingly, the absorption coefficient $k(2)$ to be obtained can be specified and set to 0.018.

As mentioned above, in novel method and apparatus in accordance with the present invention, a wide object with respect to a thin film can be measured simply and accurately. Further, no equation for a numerical operation includes any arc cosine function so that no high accuracy in the numerical operation is required.

Many widely different embodiments of the present invention may be constructed without departing from the spirit and scope of the present invention. It should be understood that the present invention is not limited to the specific embodiments described in the specification, except as defined in the appended claims.

What is claimed is:

1. A method for measuring at least one of a refractive index, an absorption coefficient and a thickness of one layer of a thin film formed on a substrate, in which the thin film has m ($m \geq 1$) layers comprising a transparent uppermost layer which is designated a first layer, in which a measured sample having the thin film and the substrate includes a total of $(3m+1)$ parameters comprising a refractive index $n(0)$ of an incident medium, a refractive index $n(j)$ ($j=1$ to $m$) of a j-th layer, absorption coefficients $k(j)$ ($j=2$ to $m$) of second to m-th layers, a refractive index $n(m+1)$ of the substrate, an absorption coefficient $k(m+1)$ of the substrate, and thickness $d(j)$ ($j=2$ to $m$) of the second to m-th layers, and in which $(3m)$ of the $(3m+1)$ parameters are known and one of the (3m+1) parameters is unknown, said method comprising the steps of:
- selectively irradiating respective monochromatic beams of s-polarized light and p-polarized light on said thin film at a predetermined incident angle;
- receiving said s-polarized light and said p-polarized light after they are reflected from said thin film and determining a reflectance Rs of said s-polarized light and a reflectance Rp of said p-polarized light on the basis of said received s-polarized and p-polarized lights;
- determining a function of F(x) including unknown parameter X as a variable by using respective values of said (3m) known parameters, a value of said incident angle $\theta(0)$, a value of wavelength $\lambda$ of said monochromatic beam, a value of said reflectance Rs and a value of said reflectance Rp;
- numerically solving an equation of F(x)=0 to thereby obtain a value of the unknown parameter X, and
- outputting a signal representing said obtained value as the value of said unknown parameter.

2. A method for measuring at least one of a refractive index, an absorption coefficient and a thickness of a thin film as claimed in claim 1, wherein said function is F(X)=a+b+c and said equation is represented by F(X)=0 and a, b and c in this function F(X) are respectively set as follows:

$$a = \rho^2(01s)\, \rho^2(12s)\, \rho^4(12p)\, \{1 - Rp\, \rho^2(01p)\}^2\, (As^2 + Bs^2) +$$

$$\rho^2(01p)\, \rho^2(12p)\, \rho^4(12s)\, \{1 - Rs\, \rho^2(01s)\}^2\, (As^2 + Bs^2) +$$

$$2\, \rho(01p)\, \rho^3(12p)\, \rho(01s)\, \rho^3(12s)\{1 - Rp\, \rho^2(01p)\}\, \{1 -$$

$$Rs\, \rho^2(01S)\}\, (ApAs + BpBp)$$

$$b = 2\, \rho^2(01s)\, \rho^2(12s)\, \rho^2(12p)\, \{\rho^{2(01p)} - Rp\}\, \{1 -$$

$$Rp\, \rho^2(01p)\}\, (As^2 + Bs2) + 2\, \rho^2(01s)\, \rho^2(12s)\, \rho^2(12p)$$

$$\{\rho^2(01p) - Rp\}\{1 - Rp\, \rho^2(01p)\}\, (As^2 + Bs^2) -$$

$$2\, \rho(01p)\, \rho(12p)\, \rho(01s)\, \rho^3(12s)\, \{\rho^2(01p) - Rp\}$$

$$\{1 - Rs\, \rho^2(01s)\}(ApAs + BpBs) -$$

$$2\, \rho(01p)\, \rho^3(12p)\, \rho(01s)\, \rho(12s)\{\rho^2(01s) - Rs\}$$

$$\{1 - Rp\, \rho^2(01p)\}\, (ApAs + BpBs) -$$

$$4\, \rho^2(01p)\, \rho^2(12p)\, \rho^2(01s)\, \rho^2(12s)\, (ApBs - BpAs)^2$$

$$c = \rho^2(01s)\, \rho^2(12s)\, (\rho^2(01p) - Rp)^2\, (As^2 + Bs^2) +$$

$$\rho^2(01p)\, \rho^2(12p)\, \{\rho^2(01s) - Rs\}^2\, (Ap^2 + Bp^2) -$$

$$2\, \rho(01p)\, \rho(12p)\, \rho(0 \cdot 1s)\, \rho(12s)\, \{\rho^2(01p) - Rp\}$$

$$\{\rho^2(01s) - Rs\}\, (ApAs + BpBs)$$

Ap, Bp As and Bs in the formulas of a, b and c are respectively set as follows;

$Ap = Rp \cos\{\phi(01p) + \phi(12p)\} - \cos\{\phi(01p) - \phi(12p)\}$ $Bp = Rp \sin\{\phi(01p) + \phi(12p)\} - \sin\{\phi(01p) - \phi(12p)\}$ $As = Rs \cos\{\phi(01s) + \phi(12s)\} - \cos\{\phi(01s) - \phi(12s)\}$ $Bs = rs \sin\{\phi(01s) + \phi(12s)\} = \sin\{\phi(01s) - \phi(12s)\}$ $\rho(01p)$, $\rho(01s)$, $\rho(12p)$, $\rho(12s)$, and $\rho(01p)$, $\phi(01s)$, $\phi(12p)$, $\phi(12s)$ in the formulas of a, b and c are respectively set as follows;

$r(01p) \equiv \rho(01p) \exp\{i\phi(01p)\}$, $r(01s) \equiv \rho(01s) \exp\{i\phi(01s)\}$, $r'(12p) \equiv \rho(12p) \exp\{i\phi(12p)\}$, $r'(12s) \equiv \rho(12s) \exp\{i\phi(12s)\}$, r(01p) and r(01s) are respectively set to amplitude reflectances of the P-polarized light and the S-polarized light on an interface between the incident medium and the first layer; and r'(12p) and r'(12s) are respectively set to amplitude reflectances of the P-polarized light and the S-polarized light provided when said monochromatic light is incident to (m−1)-thin film layers except for the first layer in the incident medium having the same refractive index as the refractive index of the first layer.

3. A method for measuring at least one of a refractive index, an absorption coefficient and a thickness of a thin film as claimed in claim 1, wherein the unknown parameter X is the refractive index of one of the layers of the thin film, the refractive index of the substrate, or the refractive index of the incident medium.

4. A method for measuring at least one of a refractive index, an absorption coefficient and a thickness of a thin film as claimed in claim 1, wherein the unknown parameter X is the absorption coefficient of the substrate or the absorption coefficient of one of the layers of the thin film other than the first layer.

5. A method of measuring at least one of a refractive index, an absorption coefficient and a thickness of a thin film formed on a substrate, said thin film having m (m ≥ 1) layers comprising a transparent uppermost layer which is designated a first layer, said method of measuring comprising the steps of;
- selecting a total of (3m+1) parameters which are measures of respective physical properties related to said film and which include a refractive index n(0) of an incident medium through which light passes before impinging on said (m) layers, a refractive index n(j) (j=1 to m) of a j-th layer of said (m) layers, absorption coefficients k(j) (j=2 to m) of a second through m-th layers of said (m) layers, a refractive index n(m+1) of the substrate, an absorption coefficient k(m+1) of the substrate and thicknesses d(j) (j=2 to m) of the second through m-th layers of said (m) layers;
- designating an arbitrary one of the (3m+1) parameters as an unknown parameter X which is a measure of a selected physical property related to said film, the other (3m) parameters being known parameters which are measures of other physical properties related to said film;
- generating monochromatic light having a wavelength $\lambda$;
- causing said monochromatic light to impinge on the thin film having said (m) layers at a predetermined incident angle $\theta(0)$ relative to said first layer after passing through said incident medium, and to be reflected from said layers as S-polarized light and P-polarized light;

measuring reflectances Rs and Rp of said S-polarized and P-polarized light;

specifying the unknown parameter X as a function $F(X)=a+b+c$ using measured values of the reflectances Rs and Rp, the wavelength $\lambda$ and (3m) known parameters;

a, b and c in this function $F(X)$ being respectively set as follows:

$$a = \rho^2(01s)\,\rho^2(12s)\,\rho^4(12p)\,\{1 - Rp\,\rho^2(01p)\}^2\,(As^2 + Bs^2) +$$

$$\rho 2(01p)\,\rho^2(12p)\,\rho^4(12s)\,\{1 - Rs\,\rho^2(01s)\}^2\,(As^2 + Bs^2) +$$

$$2\,p\,(01p)\,\rho^3(12p)\,\rho\,(01s)\,\rho^3(12s)\{1 - Rp\,\rho^2(01p)\}\,\{1 -$$

$$Rs\,\rho^2(01S)\}\,(ApAs + BpBp)$$

$$b = 2\,\rho^2(01s)\,\rho^2(12s)\,\rho^2(12p)\,\{\rho^{2(01p)-Rp}\}\,\{1 -$$

$$Rp\,\rho^2(01p)\}\,(As^2 + Bs2) + 2\,\rho^2(01s)\,\rho^2(12s)\,\rho^2(12p)$$

$$\{\rho^2(01p) - Rp\}\{1 - Rp\,\rho^2(01p)\}\,(As^2 + Bs^2) -$$

$$2\,\rho\,(01p)\,\rho\,(12p)\,\rho\,(01s)\,\rho^3(12s)\,\{\rho^2(01p) - Rp\}$$

$$\{1 - Rs\,\rho^2(01s)\}(ApAs + BpBs) -$$

$$2\,\rho\,(01p)\,\rho^3(12p)\,\rho\,(01s)\,\rho\,(12s)\{\rho^2(01s) - Rs\}$$

$$\{1 - Rp\,\rho^2(01p)\}\,(ApAs + BpBs) -$$

$$4\,\rho^2(01p)\,\rho^2(12p)\,\rho^2(01s)\,\rho^2(12s)\,(ApBs - BpAs)^2$$

$$c = \rho^2(01s)\,\rho^2(12s)\,(\rho^2(01p) - Rp)^2\,(As^2 + Bs^2) +$$

$$\rho^2(01p)\,\rho^2(12p)\,\{\rho^2(01s) - Rs\}^2\,(Ap^2 + Bp^2) -$$

$$2\,\rho\,(01p)\,\rho\,(12p)\,\rho\,(0\cdot 1s)\,\rho\,(12s)\,\{\rho^2(01p) - Rp\}$$

$$\{\rho^2(01s) - Rs\}\,(ApAs + BpBs)$$

Ap, Bp As and Bs in the formulas of a, b and c being respectively set as follows;

$Ap = Rp\cos\{\phi(01p)+\phi(12p)\} - \cos\{\phi(01p)-\phi(12p)\}$ $Bp = Rp\sin\{\phi(01p)+\phi(12p)\} - \sin\{\phi(01p)-\phi(12p)\}$ $As = Rs\cos\{\phi(01s)+\phi(12s)\} - \cos\{\phi(01s)-\phi(12s)\}$ $Bs = Rs\sin\{\phi(01s)+\phi(12s)\} = \sin\{\phi(01s)-\phi(12s)\}$ $\rho(01p)$, $\rho(01s)$, $\rho(12p)$, $\rho(12s)$, and $\phi(01p)$, $\phi(01s)$, $\phi(12p)$, $\phi(12s)$ in the formulas of a, b and c being respectively set as follows;

$r(01p) \equiv \rho(01p)\exp\{i\phi(01p)\}$, $r(01s) \equiv \rho(01s)\exp\{i\phi(01s)\}$, $r'(12p) \equiv \rho(12p)\exp\{i\phi(12p)\}$, $r'(12s) \equiv \rho(12s)\exp\{i\phi(12s)\}$, r(01p) and r(01s) being respectively set to amplitude reflectances of the P-polarized light and the S-polarized light on an interface between the incident medium and the first layer; and r'(12p) and r'(12s) are respectively set to amplitude reflectances of the P-polarized light and the S-polarized light provided when said monochromatic light is incident to (m−1)-thin film layers except for the first layer in the incident medium having the same refractive index as the refractive index of the first layer;

determining a value of said selected physical property of the film by determining said unknown parameter X through solving numerically an equation $F(X)=0$; and utilizing the value of said selected physical parameter of the film determined in said determining step.

6. A method for measuring at least one of a refractive index, an absorption coefficient and a thickness of a thin film as claimed in claim 5, wherein the unknown parameter X is the refractive index of one of the layers of the thin film, the refractive index of the substrate, or the refractive index of the incident medium.

7. A method for measuring at least one of a refractive index, an absorption coefficient and a thickness of a thin film as claimed in claim 5, wherein the unknown parameter X is the absorption coefficient of the substrate or the absorption coefficient of one of the layers of the thin film other than the first layer.

8. An apparatus for measuring at least one of a refractive index, an absorption coefficient and a thickness of a layer of a thin film formed on a substrate, in which the thin film has m (m≧1) layers comprising at least a transparent uppermost layer which is designated a first layer, in which a measured sample having the thin film and the substrate includes a total of (3m+1) parameters comprising a refractive index n(0) of an incident medium, a refractive index n(j) (j=1 to m) of a j-th layer, absorption coefficients k(j) (j=2 to m) of second to m-th layers, a refractive index n(m+1) of the substrate, an absorption coefficient k(m+1) of the substrate, and thickness d(j) (j=2 to m) of the second to m-th layers, and in which (3m) of the (3m+1) parameters are known and one of the (3m+1) parameters is unknown, said apparatus comprising:

a light source device for selectively emitting monochromatic beams of s-polarized light and p-polarized light, respectively;

a support, disposed on an optical path of said s-polarized light and said p-polarized light, for supporting said sample such that said s-polarized and p-polarized lights are respectively incident on said thin film at a predetermined incident angle;

a photo-sensor, disposed on an optical path of said s-polarized and p-polarized lights so as to receive said s-polarized light and said p-polarized light after they are reflected from said thin film, for outputting a first signal corresponding to said reflected s-polarized light and a second signal corresponding to said reflected p-polarized light;

a calculation device, electronically connected to said photo-sensor, for receiving said first signal and said second signal; and a numerical condition setting device, electrically connected to said calculation device, for setting the value of each of (3m) known parameters, a value of said incident angle $\Theta(0)$, and a value of wavelength $\lambda$ of said monochromatic beam, and for outputting respective signals corresponding to said set values, said calculation device comprising:

a reflectance determining circuit, electrically connected to said photosensor, for determining a reflectance Rs of said s-polarized light and a reflectance Rp of said p-polarized light on the basis of said first and second signals from said photo-sensor, and for outputting a third signal representing said determined reflectance Rs of said s-polarized light and a fourth signal representing said determined reflectance Rp of said p-polarized light: and an unknown parameter determining circuit, electrically connected to said numerical condition setting device and said reflectance determining circuit and storing a function of $F(n(0), n(j), k(j), d(j), \Theta(0), \lambda, Rs, Rp)$ which represents a relation among said $(3m+1)$ parameters, said incident angle, the wavelength of said monochromatic beam and reflectances of said s-polarized and p-polarized lights, for substituting values of each of said $(3m)$ known parameters, and values of said incident angle, said wavelength of said monochromatic beam and said reflectances into said function on the basis of said signals from said numerical condition setting device and third and fourth signals from said reflectance determining circuit for numerically solving an equation of $F(x)=0$ to thereby obtain a value of the unknown parameter X, and for specifying said obtained value as a value of said unknown parameter to thereby output a signal representing said specified value.

9. An apparatus for measuring at least one of a refractive index, an absorption coefficient and a thickness of a layer of a thin film formed on a substrate as claimed in claim 8, wherein said predetermined equation is represented by $F(X)=0$ and this function $F(X)$ is set to $F(X)=a+b+c$ and a, b and c in this function $F(X)$ are set as follows;

$$a = \rho^2(01s)\,\rho^2(12s)\,\rho^4(12p)\,\{1 - Rp\,\rho^2(01p)\}^2\,(As^2 + Bs^2) +$$
$$\rho^2(01p)\,\rho^2(12p)\,\rho^4(12s)\,\{1 - Rs\,\rho^2(01s)\}^2\,(Ap^2 + Bp^2) +$$
$$2\,\rho(01p)\,\rho^3(12p)\,\rho(01s)\,\rho^3(12s)\{1 - Rp\,\rho^2(01p)\}\,\{1 -$$
$$Rs\,\rho^2(01s)\}\,(ApAs + BpBp)$$

$$b = 2\,\rho^2(01s)\,\rho^2(12s)\,\rho^2(12p)\,\{\rho^{2(01p)} - Rp\}\,\{1 -$$
$$Rp\,\rho^2(01p)\}\,(As^2 + Bs^2) + 2\,\rho^2(01s)\,\rho^2(12s)\,\rho^2(12p)$$
$$\{\rho^2(01p) - Rp\}\{1 - Rp\,\rho^2(01p)\}\,(As^2 + Bs^2) -$$
$$2\,\rho(01p)\,\rho(12p)\,\rho(01s)\,\rho^3(12s)\,\{\rho^2(01p) - Rp\}$$
$$\{1 - Rs\,\rho^2(01s)\}(ApAs + BpBs) -$$
$$2\,\rho(01p)\,\rho^3(12p)\,\rho(01s)\,\rho(12s)\{\rho^2(01s) - Rs\}$$
$$\{1 - Rp\,\rho^2(01p)\}\,(ApAs + BpBs) -$$
$$4\,\rho^2(01p)\,\rho^2(12p)\,\rho^2(01s)\,\rho^2(12s)\,(ApBs - BpAs)^2$$

$$c = \rho^2(01s)\,\rho^2(12s)\,(\rho^2(01p) - Rp)^2\,(As^2 + Bs^2) +$$
$$\rho^2(01p)\,\rho^2(12p)\,\{\rho^2(01s) - Rs\}^2\,(Ap^2 + Bp^2) -$$
$$2\,\rho(01p)\,\rho(12p)\,\rho(0 \cdot 1s)\,\rho(12s)\,\{\rho^2(01p) - Rp\}$$
$$\{\rho^2(01s) - Rs\}\,(ApAs + BpBs)$$

Ap, Bp As and Bs in the formulas of a, b and c are respectively set as follows;

$Ap = Rp \cos\{\phi(01p) + \phi(12p)\} - \cos\{\phi(01p) - \phi(12p)\}$ $Bp = Rp \sin\{\phi(01p) + \phi(12p)\} - \sin\{\phi(01p) - \phi(12p)\}$ $As = Rs \cos\{\phi(01s) + \phi(12s)\} - \cos\{\phi(01s) - \phi(12s)\}$ $Bs = Rs \sin\{\phi(01s) + \phi(12s)\} - \sin\{\phi(01s) - \phi(12s)\}$ $\rho(01p)$, $\rho(01s)$, $\rho(12p)$, $\rho(12s)$, and $\phi(01p)$, $\phi(01s)$, $\phi(12p)$, $\phi(12s)$ in the formulas of a, b and c are respectively set as follows;

$r(01p) \equiv \rho(01p) \exp\{i\phi(01p)\}$, $r(01s) \equiv \rho(01s) \exp\{i\phi(01s)\}$, $r'(12p) \equiv \rho(12p) \exp\{i\phi(12p)\}$, $r'(12s) \equiv \rho(12s) \exp\{i\phi(12s)\}$, r(01p) and r(01s) being respectively set to amplitude reflectances of the P-polarized light and the S-polarized light on an interface between the incident medium and the first layer; and r'(12p) and r'(12s) being respectively set to amplitude reflectances of the P-polarized light and the S-polarized light provided when said monochromatic light is incident to $(m-1)$-thin film layers except for the first layer in the incident medium having the same refractive index as the refractive index of the first layer.

10. An apparatus for measuring at least one of a refractive index, an absorption coefficient and a thickness of a layer of a thin film formed on a substrate as claimed in claim 8, wherein the unknown parameter X is the refractive index of one of the layers of the thin filmy the refractive index of the substrate, or the refractive index of the incident medium.

11. An apparatus for measuring at least one of a refractive index, an absorption coefficient and a thickness of a layer of a thin film formed on a substrate as claimed in claim 8, wherein the unknown parameter X is the absorption coefficient of the substrate or the absorption coefficient of one of the layers of the thin film other than the first layer.

12. An apparatus for measuring at least one of a refractive index, an absorption coefficient and a thickness of a thin film formed on a substrate, said thin film having m $(m \geq 1)$ layers comprising a transparent uppermost layer which is designated a first layer, and a total of $(3m+1)$ parameters which are measures of respective physical properties and which include a refractive index $n(0)$ of an incident medium through which light passes before impinging on said (m) layers, a refractive index $n(j)$ (j=1 to m) of a j-th layer of said (m) layers, absorption coefficients $k(j)$ (j=2 to m) of second through m-th layers of said (m) layers, a refractive index $n(m+1)$ of the substrate, an absorption coefficient $k(m+1)$ of the substrate, and thickness $d(j)$ (j=2 to m) of the second through m-th layers of said (m) layers;

one of the $(3m+1)$ parameters being an unknown parameter X which is a measure of a selected physical property related to said film, the other $(3m)$ parameters being known parameters which are measures of other physical properties related to said film;

a support for supporting a measured sample;

a light source device for selectively irradiating a monochromatic beam of each of S-polarized light and P-polarized light to said measured sample at a predetermined incident angle;

a photo-sensor for receiving a light beam reflected from said measured sample and photoelectrically converting said reflected light beam;

a computer for determining a value of said selected physical property of the film by determining said unknown parameter X through calculating an equation F(X)=0 based on an output of said photosensor, this function F(X) being set to F(X)=a+b+c and a, b and c in this function F(X) being respectively set as follows:

$$a = \rho^2(01s)\,\rho^2(12s)\,\rho^4(12p)\,\{1 - Rp\,\rho^2(01p)\}^2\,(As^2 + Bs^2) +$$

$$\rho^2(01p)\,\rho^2(12p)\,\rho^4(12s)\,\{1 - Rs\,\rho^2(01s)\}^2\,(Ap^2 + Bp^2) +$$

$$2\,\rho(01p)\,\rho^3(12p)\,\rho(01s)\,\rho^3(12s)\{1 - Rp\,\rho^2(01p)\}\,\{1 -$$

$$Rs\,\rho^2(01s)\}\,(ApAs + BpBp)$$

$$b = 2\,\rho^2(01s)\,\rho^2(12s)\,\rho^2(12p)\,\{\rho^2(01p) - Rp\}\,\{1 -$$

$$Rp\,\rho^2(01p)\}\,(As^2 + Bs^2) + 2\,\rho^2(01s)\,\rho^2(12s)\,\rho^2(12p)$$

$$\{\rho^2(01p) - Rp\}\{1 - Rp\,\rho^2(01p)\}\,(As^2 + Bs^2) -$$

$$2\,\rho(01p)\,\rho(12p)\,\rho(01s)\,\rho^3(12s)\,\{\rho^2(01p) - Rp\}$$

$$\{1 - Rs\,\rho^2(01s)\}(ApAs + BpBs) -$$

$$2\,\rho(01p)\,\rho^3(12p)\,\rho(01s)\,\rho(12s)\{\rho^2(01s) - Rs\}$$

$$\{1 - Rp\,\rho^2(01p)\}\,(ApAs + BpBs) -$$

$$4\,\rho^2(01p)\,\rho^2(12p)\,\rho^2(01s)\,\rho^2(12s)\,(ApBs - BpAs)^2$$

$$c = \rho^2(01s)\,\rho^2(12s)\,(\rho^2(01p) - Rp)^2\,(As^2 + Bs^2) +$$

$$\rho^2(01p)\,\rho^2(12p)\,\{\rho^2(01s) - Rs\}^2\,(Ap^2 + Bp^2) -$$

$$2\,\rho(01p)\,\rho(12p)\,\rho(0 \cdot 1s)\,\rho(12s)\,\{\rho^2(01p) - Rp\}$$

$$\{\rho^2(01s) - Rs\}\,(ApAs + BpBs)$$

Ap, Bp As and Bs in the formulas of a, b and c being respectively set as follows;

$$Ap = Rp\cos\{\phi(01p) + \phi(12p)56 - \cos\{\phi(01p) - \phi(12p)\}$$

$$Bp = Rp\sin\{\phi(01p) + \phi(12p)\} - \sin\{\phi(01p) - \phi(12p)\}$$

$$As = Rs\cos\{\phi(01s) + \phi(12s)\} - \cos\{\phi(01s) - \phi(12s)\}$$

$$Bs = Rs\sin\{\phi(01s) + \phi(12s)\} - \sin\{\phi(01s) - \phi(12s)\}$$

$\rho(01p)$, $\rho(01s)$, $\rho(12p)$, $\rho(12s)$, and $\phi(01p)$, $\phi(01s)$, $\phi(12p)$, $\phi(12s)$ in the formulas of a, b and c being respectively set as follows;

$$r(01p) = \rho(01p)\exp\{i\phi(01p)\},$$

$$r(01s) = \rho(01s)\exp\{i\phi(01s)\},$$

$$r'(12p) = \rho(12p)\exp\{i\phi(12p)\},$$

$$r'(12s) = \rho(12s)\exp\{i\phi(12s)\},$$

r(01p) and r(01s) being respectively set to amplitude reflectances of the P-polarized light and the S-polarized light on an interface between the incident medium and the first layer;

r'(12p) and r'(12s) being respectively set to amplitude reflectances of the P-polarized light and the S-polarized light provided when said monochromatic light is incident to (m−1)-thin film layers except for the first layer in the incident medium having the same refractive index as the refractive index of the first layer; and for outputting the value of said selected physical parameter of the film.

13. An apparatus for measuring at least one of a refractive index, an absorption coefficient and a thickness of a thin film formed on a substrate as claimed in claim 12, wherein the unknown parameter X is the refractive index of one of the layers of the thin film, the refractive index of the substrate, or the refractive index of the incident medium.

14. An apparatus for measuring at least one of a refractive index, an absorption coefficient and a thickness of a thin film formed on a substrate as claimed in claim 12, wherein the unknown parameter X is the absorption coefficient of the substrate or the absorption coefficient of one of the layers of the thin film other than the first layer.

* * * * *